United States Patent
Pollack

(10) Patent No.: US 6,962,700 B1
(45) Date of Patent: Nov. 8, 2005

(54) METHOD OF MANUFACTURING IMMUNE GLOBULIN

(75) Inventor: William Pollack, Oceanside, CA (US)

(73) Assignee: Atopix Pharmaceuticals Corporation, Carlsbad, CA (US)

(*) Notice: Subject to any disclaimer, the term of this patent is extended or adjusted under 35 U.S.C. 154(b) by 141 days.

(21) Appl. No.: 09/660,862

(22) Filed: Sep. 13, 2000

(51) Int. Cl.[7] ............... A61K 39/395; A61K 45/00; C07K 16/00; C07K 1/00
(52) U.S. Cl. ............... 424/130.1; 424/85.1; 530/387.1; 530/413
(58) Field of Search ............... 530/387.1, 389.4, 530/413; 424/130.1, 85, 85.1

(56) References Cited

U.S. PATENT DOCUMENTS

| | | | |
|---|---|---|---|
| 4,089,944 A * | 5/1978 | Thomas | 424/101 |
| 4,186,192 A * | 1/1980 | Lundblad et al. | 424/85 |
| 4,322,403 A | 3/1982 | Bünnig | |
| 4,436,724 A | 3/1984 | Ohnishi | |
| 4,482,483 A | 11/1984 | Curry et al. | 260/112 R |
| 4,597,966 A * | 7/1986 | Zolton et al. | 424/85 |
| 4,639,513 A | 1/1987 | Hou | |
| 4,719,290 A | 1/1988 | Curry et al. | 530/387 |
| 5,177,194 A | 1/1993 | Sarno et al. | 530/412 |
| 5,346,687 A * | 9/1994 | Rhodes | 424/1.49 |
| 5,563,120 A | 10/1996 | Kuznetsov | |
| 5,908,827 A * | 6/1999 | Sirna | 512/12 |
| 6,069,236 A | 5/2000 | Burnouf-Radosevich et al. | 530/416 |
| 6,165,981 A * | 12/2000 | Flaa et al. | 514/21 |
| 6,281,336 B1 * | 8/2001 | Laursen et al. | 530/390.1 |

FOREIGN PATENT DOCUMENTS

EP 0205352 A2 6/1986

OTHER PUBLICATIONS

Harlow, Ed and Lane, David, Antibodies A Laboratory Manual, 1988, Cold Springs Harbor Laboratory, 287.*
Cheung et al, (Annals of Allergy, vol. 50, Mar., 1983, p. 155-160).*
Bird et al, Journal of Immunological Methods, 71, 1984, 97-105.*
Persson, Journal of Immunological Methods, 98, 91-19.*
Lambin et al, Journal of Immunological Methods, 165, 1993, p. 99-111.*

B.E. Garcia, Blocking Effect On The Release of Antigen-Specific Histamine, Journal of Investigational Allergology Clinical Immunology, vol. 3:1, pp. 26-33, Jan-Feb., 1993 (Abstract).
J. Bousquet, Combination of Passive and Active Immunization in Honeybee Venom Immunotherapy, Journal of Allergy and Clinical Immunology, vol. 79:6, pp. 947-54 (Abstract).
M.H. Lessof, Effects of Passive Antibody in Bee Venom Anaphylaxis, John Hopkins Medical Journal, vol. 142, pp. 107, Jan. 1978 (Abstract).
Lessof et al., "Effects of Passive Antibody in Been Venom Anaphylaxis," *The John Hopkins Med. J.* 142: 1-7 (1978).
Urbanek et al., "Sub-class of IgG anti-bee venom antibody produced during bee venom immunotherapy and its relationship to long-term protection from bee strings and following termination of venom immunotherapy," *Clin. Allergy* 16: 317-322 (1986).
Lessof et al., "Protection against Anaphylaxis in Hymenoptera-Sensitive Patients by Passive Immunization," *Monogr. Allergy* 12: 253-256 (Karger, Basel 1977).
Aalberse et al., "Serologic Aspecs of IgG4 Antibodies," *J. of Immunol.* 130(2): 722-723 (Feb. 1983).
Cheung et al., "Honey Bee Venom Specific Immunoglobulin G4 in Honey Bee String Allergic Patients and Bee Keepers," *Anls. Allergy* 50: 155-160 (Mar. 1983).
Schumacher et al., "Neutralization of Bee Venom Lethality by Immune Serum Antibodies," *Am. J. Trop. Med. Hyg.* 55(2): 197-201 (1996).
Van Toorenenbergen, A.W. And Aalberse, R.C. "IgG4 and Passive Sensitization of Basophil Leukocytes," *Int. Archs Allergy Appl. Immun.* 1981, pp. 432-440, vol. 65.

* cited by examiner

Primary Examiner—Lynette R. F. Smith
Assistant Examiner—Vanessa L. Ford
(74) Attorney, Agent, or Firm—Townsend and Townsend and Crew LLP

(57) ABSTRACT

A method of manufacturing hymenoptera-immune globulin is disclosed. In a presently preferred embodiment, the method involves the steps of concentrating a raw immune globulin solution; freezing the concentrated immune globulin solution; thawing the frozen concentrated immune globulin solution; adding sufficient mono or disaccharide to the thawed concentrated immune globulin solution to yield a solution of about 0.25 to about 0.35 osmolar; filtering the thawed concentrated immune globulin solution; and lyophilizing the concentrated immune globulin solution.

7 Claims, No Drawings

METHOD OF MANUFACTURING IMMUNE GLOBULIN

BACKGROUND OF THE INVENTION

1. Field of the Invention

This invention relates generally to a method for the preparation of an immune globulin suitable for intravenous use, and more particularly concerns a method of manufacturing immune globulins for treatment of type I allergies.

2. Description of Related Art

Immune globulin or immunoglobulin is commonly obtained from pooled plasma samples from donors, and typically contains IgG antibodies to various bacterial and viral infectious agents, making it useful for prophylaxis and treatment of disease, particularly in patients with compromised immune systems that make them susceptible to infections. Patients with normal immune systems may also require IgG antibodies in order to overcome certain infections that currently cannot be effectively treated with antibiotics. Many uncommon bacterial infections and viral infections against which patients may have no normal immunity can be treated by administration of immune globulins.

Hyper-immune serum globulin is obtained from plasma from donors selected for high titers of specific antibodies, and has been used to prevent hepatitis B, tetanus, rabies, and varicella-zoster as well as to prevent immunization to the Rh-factor in Rh-negative mothers. Individuals who have recovered from bacterial illnesses typically develop antibodies that can confer immunity in others to the illness.

Antitoxins have been shown to be of great value in treating patients envenomated by bacterial toxins or from the bites of venomous snakes or stings of insects. Such antivenins were mostly derived from the serum of immunized horses but are today almost exclusively obtained from the plasma of immune donors from which the antibody or antibodies are removed. Such antibodies occur in the gamma globulin. A small portion of the population is extremely sensitive (allergic) to the stings of flying insects, especially honey bees, wasps, hornets and yellow jackets (the hymenoptera). The advance of aggressive Africanized or so-called "killer" bees has also increased risks for the general population from multiple bee stings and especially for individuals highly allergic to bee venom. In view of these risks, it is desirable to provide a relatively inexpensive method for manufacturing immune globulins that can provide protection against serious life threatening allergic reactions such as anaphylaxis and/or can be used as an antitoxin to neutralize the toxic properties of the venoms and prevent "end organ" damage, thus possibly saving the life of the victim of the stings. Intravenous administration of immune globulin allows the desired level of circulating antibody to be reached quickly. However, intravenous injections of many immune globulin products can lead to reactions that are caused by aggregation and fragmentation of the immune globulin which forms during the fractionation and preparation of the product. It is desirable, therefore, to provide a method of manufacture of immune globulins that is safe and effective, meeting current standards for sterility and pyrogenicity. The present invention meets these needs.

SUMMARY OF THE INVENTION

Briefly, and in general terms, the present invention provides for a method of manufacture of immune globulins that is safe and effective, meeting current standards for sterility, pyrogenicity, residual moisture, and general safety.

In a presently preferred embodiment, the present invention provides for a method of manufacturing immune globulins that comprises the steps of concentrating the raw immune globulin solution; freezing the concentrated immune globulin solution; thawing the frozen concentrated immune globulin solution; adding sufficient glucose to the thawed concentrated immune globulin solution to yield an osmolarity of about 0.25 to about 0.35 osmolar; filtering the thawed concentrated immune globulin solution; and lyophilizing the concentrated immune globulin solution. In a presently preferred embodiment, the raw immune globulin is provided by fractionating a sterile, purified donor plasma pool to provide a raw immune globulin solution; adding sodium chloride to the raw immune globulin solution to a final molarity in the range of about 0.03 to 0.05M. In another preferred aspect of the method, the method further involves providing a sterilized donor blood plasma pool; purifying the donor blood plasma pool; adjusting the pH of the purified donor plasma pool to about 6.5; adjusting the conductivity of the purified donor plasma pool to a range of about 3.5 to 6.0 millisiemens. The sterilized donor blood plasma pool is preferably from immune donors. In a presently preferred aspect, the donor plasma is treated with a virucide. In a currently preferred embodiment, the step of purifying the donor blood plasma pool comprises treating the sterilized donor blood plasma pool with microcrystalline silica, followed by separating the immune globulin solution from the microcrystalline silica to yield a clarified donor plasma pool. In another presently preferred aspect of the method, the step of concentrating the raw immune globulin solution comprises concentrating the solution by ultrafiltration.

The above methods have been found to produce an immune globulin product that is safe and effective for the treatment of Type I allergies. Furthermore, the methods disclosed produce a product that meets current standards for sterility and pyrogenicity. These and other aspects and advantages of the invention will become apparent from the following detailed description which illustrates, by way of example, the features of the invention.

DETAILED DESCRIPTION OF THE PREFERRED EMBODIMENTS

Although antitoxins and antivenins have been developed and used for years, it is important that any immune globulins for prevention or treatment of reactions due to bee stings be safe and effective, meeting current standards for sterility, pyrogenicity, residual moisture, and general safety, to avoid severe reactions that may be caused by the immune globulins themselves.

In the method for manufacturing immune globulins according to the present invention, a pool of virucide-treated donor plasma is first assembled, typically from donors who already have hyper immune serum globulin. An aliquot pool of the plasma units is made typically to equal about 10 mL, prior to pooling, based on the original volumes or weights of the plasma bags.

It is then necessary to determine the total IgG of the aliquot pool, the total IgG4 of the aliquot pool, the total antibody in the aliquot pool, and the proportion or percentage of blocking antibody in the IgG4 fraction in the aliquot pool. The determination of the total IgG of the aliquot pool is preferably performed by a sensitive technique for detecting and measuring antibodies in a solution, such as an enzyme-linked immunosorbent assay (ELISA) method, and/ or Radial Immune Diffusion (RID) method, whichever give the most reproducible and accurate data against known standards. The total IgG4 of the aliquot pool can also be determined similarly by ELISA or RID methods. The total antibody can similarly by determined either by ELISA, or a radioimmunoassay (RIA) or RAST tests, providing the latter can be standardized for true quantitative determinations of specific antibodies.

It is important to obtain the most accurate and sensitive assay of the proportion or percentage of the anti-venom in the IgG4 fraction. The best method is an ELISA technique that reacts with bee-venom specific antibody of the plasma pool. This technique requires comparison with an anti-total IgG. An acceptable alternative is the determination of the ratio of diffusion of the IgG and IgG4 in RID plates. The purpose of this analysis is to compare the final IgG4 preparation in order to estimate losses and costs of production. These tests are required because IgG4 offers a unique ability to provide blocking antibody with known freedom from any ability of the antibody to bind to mast cells and basophiles, unlike IgG 1, IgG2 and IgG3, which have low affinity receptors for these important allergy mediator cells. Pure IgG4 blocking antibody has not been used before for this purpose.

Later in the method, the same series of tests are required on the fractionated globulin, first as a confirmation of the tests performed on the donor plasma, but also to estimate the dosage and vialing requirements and to estimate the costs of manufacturing. Other tests on the globulin preparations are really standard Good Manufacturing Practices (GMP). These in summary are: a) acute toxicology in two rodents; b) pyrogen tests by the Limulus method; c) sterility tests after sterile filtration and before vialing and lyophilization; d) total protein by Kjeldahl or other suitable methods; e) protein electrophoresis; f) total purity analysis for any contaminating proteins or other impurities; g) gel filtration for determination of split products or polymers; h) analysis for viral contaminants, e.g. HIV, HBV, HCV etc. by the most sensitive methods, extant; and i) other tests required by the FDA and in the Federal Register.

Preparation of Blocking-Antibody Plasma Pool

Following testing of the donor plasma pool, the donor plasma pool is typically frozen for storage until it is time for further processing of the donor plasma pool. The plasma units selected from prior antibody analysis (usually 600 to 800 milliliters each), that are to constitute the final plasma pool to be fractionated, are removed from the freezer and allowed to thaw at approximately 5° C. for 48–72 hours.

The plasma units are then pooled into a sterile container under aseptic conditions in a class 100 or less clean room or laboratory air-flow containment area. The weight of the plasma pool is then measured to obtain the total volume.

The plasma should be treated in accordance with a virucidal method, such as the "solvent-detergent" method of the New York Blood Bank or by careful heating to 60° C. Whatever method is used to sterilize the plasma pool, the plasma should be treated to make it comparable to the original plasma in terms of its suitability for fractionation by the method to be described. For example, it is necessary that the final post-sterilized pool have the same pH and ionic strength (as judged by conductivity measurements) as the original pre-sterilized pool of plasma.

The sterilized plasma pool is then treated by adding approximately 7 grams of microcrystalline silica (Aerosil 200) per liter of the pool. The Aerosil is previously sterilized at about 180°–185° C. for at least 4 hours in a hot air oven. The addition of the Aerosil to the plasma should be done aseptically. The plasma should then be stirred slowly (so as not to create foaming) for about 1 hour at room temperature under aseptic conditions.

The suspension is then centrifuged at about 3000×g for about 30 minutes at 2–8° C. degrees centigrade. The supernate is carefully decanted into a large sterile and depyrogenated container. The Aerosil pellet is then resuspended in a volume, equivalent to 14% of the starting volume of the plasma, of pyrogen-free 0.9% sodium chloride solution. After mixing, the suspension is centrifuged at about 3000 g for 30 minutes at 2–8° C., maintaining sterility throughout the procedure. The supernates are then combined and the plasma pool is clarified by passage of the plasma pool through a sterile Millipore AW 19 pre-filter, or equivalent membrane. The conductivity of a small sample of the filtered pool should then be determined and the bulk solution diluted with sterile pyrogen-free distilled water to reach a conductivity of 3.5 to 6.0 millisiemens, after the addition of N/10 HCl to bring the pH to 6.5.

Fractionation of the Plasma Pool

The fractionation method described requires the passage of the plasma through anionic and cationic resin beds. It is recognized that there are several alternative choices that can accomplish the aim of separating in pure form clinically effective IgG4. The method described in detail that follows is the presently preferred one.

The diluted plasma is passed through a suitable size bed (16–50 L) of DEAE-sepharose (CL-6B) which has been equilibrated with 0.025 M sodium phosphate at pH 6.5. The material is pumped through the bed at the rate of about 175 mL/minute. The plasma should then be followed with 0.025M sodium phosphate pH 6.5. The pH 6.5 buffer solution contains 0.653 gm $Na_2HPO_4.H_2O$ and 2.855 gm of $NaH_2PO_4.H_2O$ per liter of distilled water (Pyrogen free) at 25° C. The effluent is preferably monitored at 280 nM with a suitable instrument, such as the Pharmacia Single Path Monitor UV-1. The effluent can be collected when the UV trace on the recorder indicates a sharp rise in absorbency, and collection is continued until the absorbency drops to about 5% of the peak value.

The effluent is maintained at pH 6.5, and is passed directly through a similarly prepared, but about one third the column volume, of CM-sepharose (CL6B) equilibrated to pH 6.5 with 0.025 M sodium phosphate buffer as above. The material is pumped through the column as before, at about 175 mL/minute. The protein solution should then be followed with 0.025 M sodium phosphate at pH 6.5.

The effluent is then monitored as before at 280 nM with a suitable instrument, and the effluent should begin to be collected when the UV trace on the recorder indicates a sharp rise in absorbency. Collection should be continued until the absorbency drops to about 5% of the peak value. This effluent is mostly, if not entirely, IgG4. The resin beds as well as the buffer solutions and collecting vessels should be pyrogen-free and sterilized by autoclaving.

Sodium chloride (sterilized and pyrogen-free) is then added to a final level of 0.03 to 0.05M, and the effluent immune globulin is concentrated, preferably by ultrafiltration with a suitable apparatus, such as the Millipore Cassette System with a 10,000 nominal molecular weight cut-off membrane (PTGC 000 05 ca No). The filtration rate is about 425 mL/minute and the approximate inlet and outlet pressures are 16 psi and 10 psi respectively. When the starting volume has been reduced about 70-fold, the cassette is flushed with about 300–500 mL of 0.05M sodium chloride solution, and this is added to the immune globulin concentrate. The solution is then frozen and maintained at −30° C.

or lower. The solution is then thawed, and sufficient sterile and pyrogen-free lactose is added to the bulk solution to result in a solution of about 0.25 to 0.35 osmolar. The concentrated immune globulin is then sterile filtered through a 0.22 micron membrane filter, and stored at about −11° C. or colder until vialing and lyophilization.

Vial Filling and Freeze Drying

The sample is then thawed at about 5° C., and filtered through a 0.22 micron filter. Samples are removed for tests of sterility, pyrogenicity and potency. Following successful testing, the vials are filled aseptically at a specified fill volume of bulk solution. The vials are subjected to a standard freeze-dry cycle, and the chamber is restored to atmospheric pressure with sterile nitrogen. The freeze-drying cycle is dependent on the apparatus used or the vendor used if this work is sub-contracted.

Samples are obtained for moisture determination during drying of the product at full vacuum at the terminal drying temperature. After acceptable moisture results have been obtained, the chamber should be restored to atmospheric pressure with sterile nitrogen. Within the lyophilizer, the freeze-dried vials should be aseptically stopped and sealed.

The results of these methods is the production of an immune globulin of high effectiveness and safety for the treatment of a wide range of Type I allergies while maintaining current standards for sterility and pyrogenicity.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of manufacturing IgG4 immune globulin that has a decreased risk of aggregation and fragmentation, said method comprising:
   (a) adjusting plasma to a pH of 6.5 and a conductivity of between 3.5 to 6 millisiemens, thereby obtaining a diluted plasma;
   (b) contacting the diluted plasma of step (a) with an anion exchange resin to obtain an anion exchange effluent; and
   (c) contacting the effluent of step (b) with a cation exchange resin to obtain a cation exchange effluent that comprises IgG4 essentially free of other IgG subtypes.

2. The method of claim 1, further comprising the steps of:
   (d) adding NaCl to a final concentration of 0.03 to 0.05 M NaCl;
   (e) filtering the solution of step (d);
   (f) centrifuging the filtrate of step (e);
   (g) freezing the supernatant of step (f);
   (h) thawing the frozen supernatant of step (g);
   (i) adding a monosaccharide or disaccharide to the thawed supernatant of step (h) to a final osmolarity of between 0.22 to 0.35 OsM;
   (j) filtering the solution of step (i);
   (k) freezing the filtered solution of step (j);
   (l) thawing the frozen solution of step (k); and
   (m) lyophilizing the solution of step (1).

3. The method of claim 1, wherein said plasma is plasma obtained from an immune donor.

4. The method of claim 1, wherein said anion exchange resin comprises Sepharose and a diethyl aminoethyl ion exchange group.

5. The method of claim 1, wherein said cation exchange resin comprises Sepharose and a carboxy methyl ion exchange group.

6. The method of claim 1, wherein said cation exchange effluent consists essentially of IgG4.

7. The method of claim 2, wherein said monosaccharide is lactose.

* * * * *